(12) United States Patent
Li et al.

(10) Patent No.: US 8,588,878 B2
(45) Date of Patent: Nov. 19, 2013

(54) SIMULTANEOUS MEASUREMENT OF PULSE AND REGIONAL BLOOD OXYGEN SATURATION

(75) Inventors: Youzhi Li, Longmont, CO (US); Bo Chen, Louisville, CO (US); Edward M. McKenna, Boulder, CO (US); Paul Stanley Addison, Edinburgh (GB)

(73) Assignee: Covidien LP, Mansfield, MA (US)

( * ) Notice: Subject to any disclaimer, the term of this patent is extended or adjusted under 35 U.S.C. 154(b) by 455 days.

(21) Appl. No.: 12/944,945

(22) Filed: Nov. 12, 2010

(65) Prior Publication Data
US 2011/0112387 A1 May 12, 2011

Related U.S. Application Data

(60) Provisional application No. 61/260,741, filed on Nov. 12, 2009.

(51) Int. Cl.
*A61B 5/1455* (2006.01)

(52) U.S. Cl.
USPC .......................................... 600/323; 600/336

(58) Field of Classification Search
USPC ........................... 600/310, 322, 323, 324, 336
See application file for complete search history.

(56) References Cited

U.S. PATENT DOCUMENTS

| | | | |
|---|---|---|---|
| 5,902,235 A | 5/1999 | Lewis et al. | |
| 6,587,703 B2 | 7/2003 | Cheng et al. | |
| 6,615,065 B1 | 9/2003 | Barrett et al. | |
| 6,714,804 B2 | 3/2004 | Al-Ali et al. | |
| 6,898,452 B2 | 5/2005 | Al-Ali et al. | |
| 7,865,223 B1 * | 1/2011 | Bernreuter | 600/323 |
| 2007/0149864 A1 | 6/2007 | Laakkonen | |
| 2008/0316488 A1 | 12/2008 | Mao et al. | |

OTHER PUBLICATIONS

Addison, Paul S., The Illustrated Wavelet Transform Handbook, Taylor & Francis Group, 2002, pp. 1-353.

* cited by examiner

*Primary Examiner* — Eric Winakur
(74) *Attorney, Agent, or Firm* — Shvarts & Leiz LLP

(57) ABSTRACT

Methods and systems are provided that allow for the simultaneous calculation of pulse and regional blood oxygen saturation. An oximeter system that includes a sensor with a plurality of emitters and detectors may be used to calculate a pulse and/or regional blood oxygen saturation. A plurality of light signals may be emitted from light emitters. A first light signal may be received at a first light detector and a second light signal may be received at a second light detector. A pulse and/or regional blood oxygen saturation value may be calculated based on the received first and/or second light signals. The pulse and regional blood oxygen saturation values may be calculated substantially simultaneously. The calculated pulse and regional blood oxygen saturation values as well as other blood oxygen saturation values may be displayed simultaneously in a preconfigured portion of a display.

20 Claims, 6 Drawing Sheets

US 8,588,878 B2

SIMULTANEOUS MEASUREMENT OF PULSE AND REGIONAL BLOOD OXYGEN SATURATION

CROSS REFERENCE TO RELATED APPLICATION

This application claims the benefit of U.S. Provisional Application No. 61/260,741, filed Nov. 12, 2009, which is hereby incorporated by reference in its entirety.

SUMMARY

The present disclosure relates to signal processing and, more particularly, the present disclosure relates to calculating both pulse and regional blood oxygen saturation values.

In an embodiment, a plurality of light signals may be emitted from light emitters. A first light signal of the plurality of light signals may be received at a first light detector. A second light signal of the plurality of light signals may be received at a second light detector. A pulse blood oxygen saturation may be calculated based on the received first light signal using a processor. A regional blood oxygen saturation may be calculated based on the received first light signal and the received second light signal. The pulse blood oxygen saturation and the regional blood oxygen saturation may be calculated substantially simultaneously.

In an embodiment, pulse blood oxygen saturation may be calculated based on the intensities of two wavelengths of light signals (e.g., RED and IR light emitted and received) at different points in a pulse cycle (e.g., as the volume of blood in a pulsing tissue, such as the arteries, changes). Regional blood oxygen saturation may be simultaneously calculated by analyzing the intensities (e.g., emitted and received) of two wavelengths of light to determine the blood oxygen saturation within the venous, arterial and capillary systems within a region of a patient.

In an embodiment, a sensor including two emitters and two detectors may be used to simultaneously calculate the pulse blood oxygen saturation and the regional blood oxygen saturation. One detector that may be relatively "close" to the two emitters and another detector may be relatively "far" from the two emitters. The emitters may periodically emit light signals at two or more wavelengths (e.g., RED and IR light) for varying durations. Based on the emitted light from the emitters, the received light at the "close" detector, and/or at the "far" detector, pulse blood oxygen saturation and regional blood oxygen saturation may be simultaneously calculated. For example, the pulse blood oxygen saturation may be calculated based on a "ratio-of-ratios" technique and the regional blood oxygen saturation may be calculated based on a light intensity differencing technique. The calculated pulse and regional blood oxygen saturation values as well as other values derived from the pulse and/or regional blood oxygen saturation may be displayed simultaneously in a preconfigured portion of a display.

BRIEF DESCRIPTION OF THE DRAWINGS

The above and other features of the present disclosure, its nature and various advantages will be more apparent upon consideration of the following detailed description, taken in conjunction with the accompanying drawings in which.

DETAILED DESCRIPTION

Figure 1:
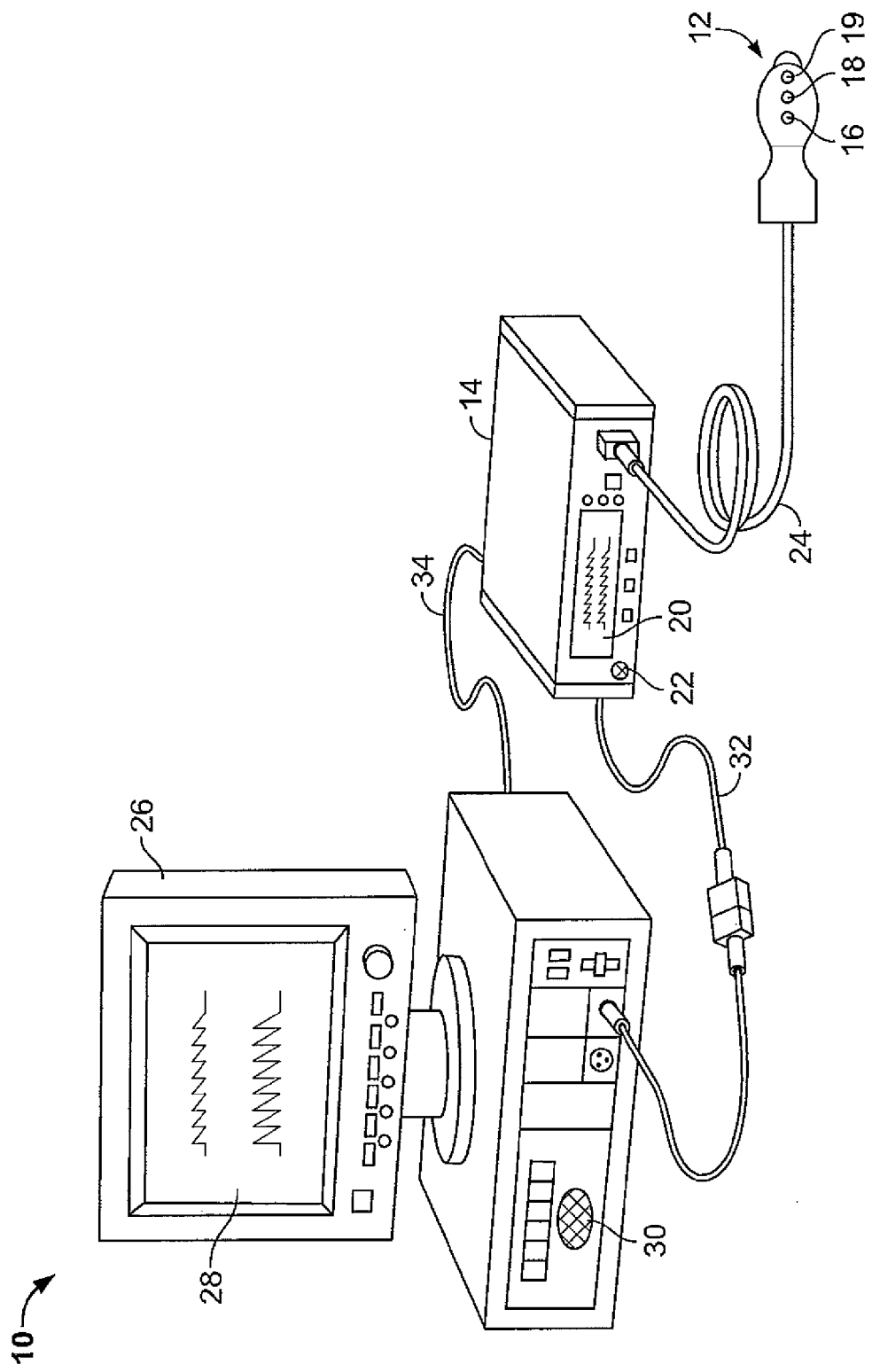
FIG. 1 shows an illustrative oximetry system in accordance with an embodiment.

An oximeter is a medical device that may determine the oxygen saturation of blood. An oximeter may include a light sensor that is placed at a site on a patient, typically a fingertip, toe, forehead or earlobe, or in the case of a neonate, across a foot. The oximeter may pass light using a light source through blood perfused tissue and photoelectrically sense the absorption of light in the tissue. For example, the oximeter may measure the intensity of light that is received at the light sensor as a function of time. A signal representing light intensity versus time or a mathematical manipulation of this signal (e.g., a scaled version thereof, a log taken thereof, a scaled version of a log taken thereof, etc.) may be referred to as the photoplethysmograph (PPG) signal. In addition, the term "PPG signal," as used herein, may also refer to an absorption signal (i.e., representing the amount of light absorbed by the tissue) or any suitable mathematical manipulation thereof. The light intensity or the amount of light absorbed may then be used to calculate the amount of the blood constituent (e.g., oxyhemoglobin) being measured and other physiological parameters such as the pulse rate and when each individual pulse occurs.

The light passed through the tissue is selected to be of one or more wavelengths that are absorbed by the blood in an amount representative of the amount of the blood constituent present in the blood. The amount of light passed through the tissue varies in accordance with the changing amount of blood constituent in the tissue and the related light absorption. Red (RED) and infrared (IR) wavelengths may be used because it has been observed that highly oxygenated blood will absorb relatively less red light and more infrared light than blood with a lower oxygen saturation. The light can be generated and transmitted into the tissue in any one of many known ways, for example, an LED placed near to the tissue, or an LED placed at a distance from the tissue, with an optical fiber to transmit the light to the tissue, or a broadband light source used in either of these configurations.

It will be understood that, as used herein, the term "light" may refer to energy produced by radiative sources and may include one or more of ultrasound, radio, microwave, millimeter wave, infrared, visible, ultraviolet, gamma ray or X-ray electromagnetic radiation. As used herein, light may also include any wavelength within the radio, microwave, infrared, visible, ultraviolet, or X-ray spectra, and that any suitable wavelength of electromagnetic radiation may be appropriate for use with the present techniques.

When the measured blood parameter is the oxygen saturation of hemoglobin, a convenient starting point assumes a saturation calculation based on Lambert-Beer's law. The following notation will be used herein:

$$I(\lambda,t)=I_o(\lambda)\exp(-(s\beta_o(\lambda)+(1-s)\beta_r(\lambda))l(t)) \quad (1)$$

where:
λ=wavelength;
t=time;
I=intensity of light detected;
$I_o$=intensity of light transmitted;
s=oxygen saturation;
$\beta_o, \beta_r$=empirically derived absorption coefficients; and
l(t)=a combination of concentration and path length from emitter to detector as a function of time.

One common type of oximeter is a pulse oximeter, which may indirectly measure the oxygen saturation of a patient's blood (as opposed to measuring oxygen saturation directly by analyzing a blood sample taken from the patient) and changes in blood volume in the skin. In pulse oximetry, by comparing the intensities of two wavelengths at different points in the pulse cycle, it is possible to estimate the blood oxygen saturation of hemoglobin in arterial blood. Ancillary to the blood oxygen saturation measurement, pulse oximeters may also be used to measure the pulse rate of the patient. Pulse oximeters typically measure and display various blood flow characteristics including, but not limited to, the oxygen saturation of hemoglobin in arterial blood.

For example, using a pulse oximeter, saturation may be calculated by solving for the "ratio of ratios" as follows.

1. First, the natural logarithm of (1) is taken ("log" will be used to represent the natural logarithm) for IR and Red $$\log I = \log I_o - (s\beta_o + (1-s)\beta_r)l \quad (2)$$

2. (2) is then differentiated with respect to time $$\frac{d\log I}{dt} = -(s\beta_O + (1-s)\beta_r)\frac{dl}{dt} \quad (3)$$

3. Red (3) is divided by IR (3)

$$\frac{d\log I(\lambda_R)/dt}{d\log I(\lambda_{IR})/dt} = \frac{s\beta_O(\lambda_R)+(1-s)\beta_r(\lambda_R)}{s\beta_O(\lambda_{IR})+(1-s)\beta_r(\lambda_{IR})} \quad (4)$$

4. Solving for s $$s = \frac{\frac{d\log I(\lambda_{IR})}{dt}\beta_r(\lambda_R) - \frac{d\log I(\lambda_R)}{dt}\beta_R(\lambda_{IR})}{\frac{d\log I(\lambda_R)}{dt}(\beta_O(\lambda_{IR})-\beta_r(\lambda_{IR})) - \frac{d\log I(\lambda_{IR})}{dt}(\beta_O(\lambda_R)-\beta_r(\lambda_R))}$$

Note in discrete time $$\frac{d\log I(\lambda, t)}{dt} \simeq \log I(\lambda, t_2) - \log I(\lambda, t_1)$$

Using log A-log B=log A/B, $$\frac{d\log I(\lambda, t)}{dt} \simeq \log\left(\frac{I(t_2,\lambda)}{I(t_1,\lambda)}\right)$$

So, (4) can be rewritten as $$\frac{\frac{d\log I(\lambda_R)}{dt}}{\frac{d\log I(\lambda_{IR})}{dt}} \simeq \frac{\log\left(\frac{I(t_1,\lambda_R)}{I(t_2,\lambda_R)}\right)}{\log\left(\frac{I(t_1,\lambda_{IR})}{I(t_2,\lambda_{IR})}\right)} = R \quad (5)$$

where R represents the "ratio of ratios." Solving (4) for s using (5) gives $$s = \frac{\beta_r(\lambda_R) - R\beta_r(\lambda_{IR})}{R(\beta_O(\lambda_{IR})-\beta_r(\lambda_{IR})) - \beta_O(\lambda_R) + \beta_r(\lambda_R)}.$$

From (5), R can be calculated using two points (e.g., PPG maximum and minimum), or a family of points. One method using a family of points uses a modified version of (5). Using the relationship $$\frac{d\log I}{dt} = \frac{dI/dt}{I} \quad (6)$$

now (5) becomes $$\frac{\frac{d\log I(\lambda_R)}{dt}}{\frac{d\log I(\lambda_{IR})}{dt}} \simeq \frac{\frac{I(t_2,\lambda_R)-I(t_1,\lambda_R)}{I(t_1,\lambda_R)}}{\frac{I(t_2,\lambda_{IR})-I(t_1,\lambda_{IR})}{I(t_1,\lambda_{IR})}} = \quad (7)$$

$$\frac{[I(t_2,\lambda_R)-I(t_1,\lambda_R)]I(t_1,\lambda_{IR})}{[I(t_2,\lambda_{IR})-I(t_1,\lambda_{IR})]I(t_1,\lambda_R)} = R$$

which defines a cluster of points whose slope of y versus x will give R where $$x(t)=[I(t_2,\lambda_{IR})-I(t_1,\lambda_{IR})]I(t_1,\lambda R)$$

$$y(t)=[I(t_2,\lambda_R)-I(t_1,\lambda_R)]I(t_1,\lambda IR)$$

$$y(t)=Rx(t) \quad (8)$$

Once R is determined or estimated, for example, using the techniques described above, the blood oxygen saturation can be determined or estimated using any suitable technique for relating a blood oxygen saturation value to R. For example, blood oxygen saturation can be determined from empirical data that may be indexed by values of R, and/or it may be determined from curve fitting and/or other interpolative techniques.

The foregoing is merely illustrative and any suitable processing techniques may be used to calculate pulse oximetry values. For example, Fourier transforms and continuous wavelet transforms may be used to process the PPG signals and derive blood oxygen saturation.

A regional oximeter is another common type of oximeter, which may be used to calculate an oxygen saturation of a patient's blood in a non-invasive manner. In regional oximetry, by comparing the intensities of two or more wavelengths of light, it is possible to estimate the blood oxygen saturation of hemoglobin in a region of a body. Specifically, two, three, four or more wavelengths may be used. Whereas pulse oximetry measures blood oxygen based on changes in the volume of blood due to pulsing tissue (e.g., arteries), regional oximetry examines blood oxygen saturation within the venous, arterial and capillary systems within a region of a patient. For example, a regional oximeter may include a sensor to be placed on a patient's forehead and may be used to calculate the oxygen saturation of a patient's blood within the venous, arterial and capillary systems of a region underlying the patient's forehead (e.g., in the cerebral cortex). The sensor may include two emitters and two detectors: one detector that is relatively "close" to the two emitters and another detector that is relatively "far" from the two emitters.

For example, if $I_A$ represents the intensity of the received/detected light associated with the "close" detector, $$\frac{I_A(\lambda, t)}{I_O(\lambda)},$$

may be derived using Lambert-Beer's law, described above. Similarly, if $I_B$ represents the intensity of the received/detected light associated with the "far" detector, $$\frac{I_B(\lambda, t)}{I_O(\lambda)},$$

may be derived using Lambert-Beer's law, described above. Light intensity of multiple wavelengths may be received at both the "close" and the "far" detectors. For example, if two wavelength were used, the two wavelengths may be contrasted at each location and the resulting signals may be contrasted to arrive at a regional saturation value that pertains to additional tissue through which the light received at the "far" detector passed (tissue in addition to the tissue through which the light received by the "close" detector passed, e.g., the brain tissue), when it was transmitted through a region of a patient (e.g., a patient's cranium). Other methods to calculate regional blood oxygen saturation are well known in the art.

In view of the foregoing, while pulse oximeters and regional oximeters both calculate blood oxygen saturation, they typically perform different calculations on the PPG signals to obtain the saturation values. In both types of oximeters, the PPG signals typically undergo pre-processing (e.g., filtering, equalizing, weighting, analog-to-digital conversion) prior to the calculation of blood oxygen saturation. Because pulse and regional oximeters typically analyze the PPG signals differently, the pre-processing that is used for one may not provide good results for the other. For example, in pulse oximetry, it may desirable for the pre-processing to keep and clean up the pulsatile portion of the PPG signal. However, in regional oximetry, the pulsatile component of the PPG signal may not be important and the pre-processing may remove portions of the pulsatile portion.

In accordance with the present disclosure, pulse oximetry and regional oximetry may be performed simultaneously using one or more common sensors. Using at least one sensor, which has one or more emitters and one or more detectors, it is possible to calculate both pulse and regional blood oxygen saturation simultaneously. In an embodiment, RED and IR light may be sequentially emitted by the emitter(s) and may be detected by the detectors. In another embodiment, a broadband light signal may be emitted by the emitter(s) and may be detected. In an embodiment, the light intensity and/or duration that is emitted by the emitter(s) may be different for the pulse blood oxygen saturation calculation and the regional blood oxygen saturation calculation. In an embodiment, the light signal received at one of the detectors may be used in the calculation of both pulse and regional blood oxygen saturation. The received light may undergo different pre-processing for the pulse and regional blood oxygen saturation calculations. Pulse and regional blood oxygen saturation may also be simultaneously calculated using any number of emitters and any number of detectors in a similar fashion.

FIG. 1 is a perspective view of an embodiment of an oximetry system 10. System 10 may include a sensor 12 and an oximetry monitor 14. Sensor 12 may include emitters 16 for emitting light at two or more wavelengths into a patient's tissue. Two detectors 18 and 19 may also be provided in sensor 12 for detecting the light originally from emitters 16 that emanates from the patient's tissue after passing through the tissue.

According to an embodiment and as will be described, system 10 may include a plurality of sensors forming a sensor array in lieu of single sensor 12. Each of the sensors of the sensor array may be a complementary metal oxide semiconductor (CMOS) sensor. Alternatively, each sensor of the array may be charged coupled device (CCD) sensor. In another embodiment, the sensor array may be made up of a combination of CMOS and CCD sensors. The CCD sensor may comprise a photoactive region and a transmission region for receiving and transmitting data whereas the CMOS sensor may be made up of an integrated circuit having an array of pixel sensors. Each pixel may have a photodetector and an active amplifier.

According to an embodiment, emitters 16 and detectors 18 and 19 may be on opposite sides of a digit such as a finger or toe, in which case the light that is emanating from the tissue has passed completely through the digit. In an embodiment, emitters 16 and detectors 18 and 19 may be arranged so that light from emitters 16 penetrates the tissue and is reflected by the tissue into detectors 18 and 19, such as a sensor designed to obtain oximetry data from a patient's forehead.

In an embodiment, the sensor or sensor array may be connected to and draw its power from monitor 14 as shown. In another embodiment, the sensor may be wirelessly connected to monitor 14 and include its own battery or similar power supply (not shown). Monitor 14 may be configured to calculate physiological parameters based at least in part on data received from sensor 12 relating to light emission and detection. In an alternative embodiment, the calculations may be performed on the monitoring device itself and the result of the oximetry reading may be passed to monitor 14. Further, monitor 14 may include a display 20 configured to display the physiological parameters or other information about the system. In the embodiment shown, monitor 14 may also include a speaker 22 to provide an audible sound that may be used in various other embodiments, such as for example, sounding an audible alarm in the event that a patient's physiological parameters are not within a predefined normal range.

In an embodiment, sensor 12, or the sensor array, may be communicatively coupled to monitor 14 via a cable 24. However, in other embodiments, a wireless transmission device (not shown) or the like may be used instead of or in addition to cable 24.

In the illustrated embodiment, oximetry system 10 may also include a multi-parameter patient monitor 26. The monitor may be cathode ray tube type, a flat panel display (as shown) such as a liquid crystal display (LCD) or a plasma display, or any other type of monitor now known or later developed. Multi-parameter patient monitor 26 may be configured to calculate physiological parameters and to provide a display 28 for information from monitor 14 and from other medical monitoring devices or systems (not shown). For example, multiparameter patient monitor 26 may be configured to display an estimate of a patient's blood oxygen saturation generated by pulse oximetry monitor 14 (referred to as an "SpO$_2$" measurement), regional blood oxygen saturation generated by oximetry monitor 14, pulse rate information from monitor 14 and blood pressure from a blood pressure monitor (not shown) on display 28.

Monitor 14 may be communicatively coupled to multi-parameter patient monitor 26 via a cable 32 or 34 that is coupled to a sensor input port or a digital communications port, respectively and/or may communicate wirelessly (not shown). In addition, monitor 14 and/or multi-parameter patient monitor 26 may be coupled to a network to enable the sharing of information with servers or other workstations (not shown). Monitor 14 may be powered by a battery (not shown) or by a conventional power source such as a wall outlet.

Figure 2:
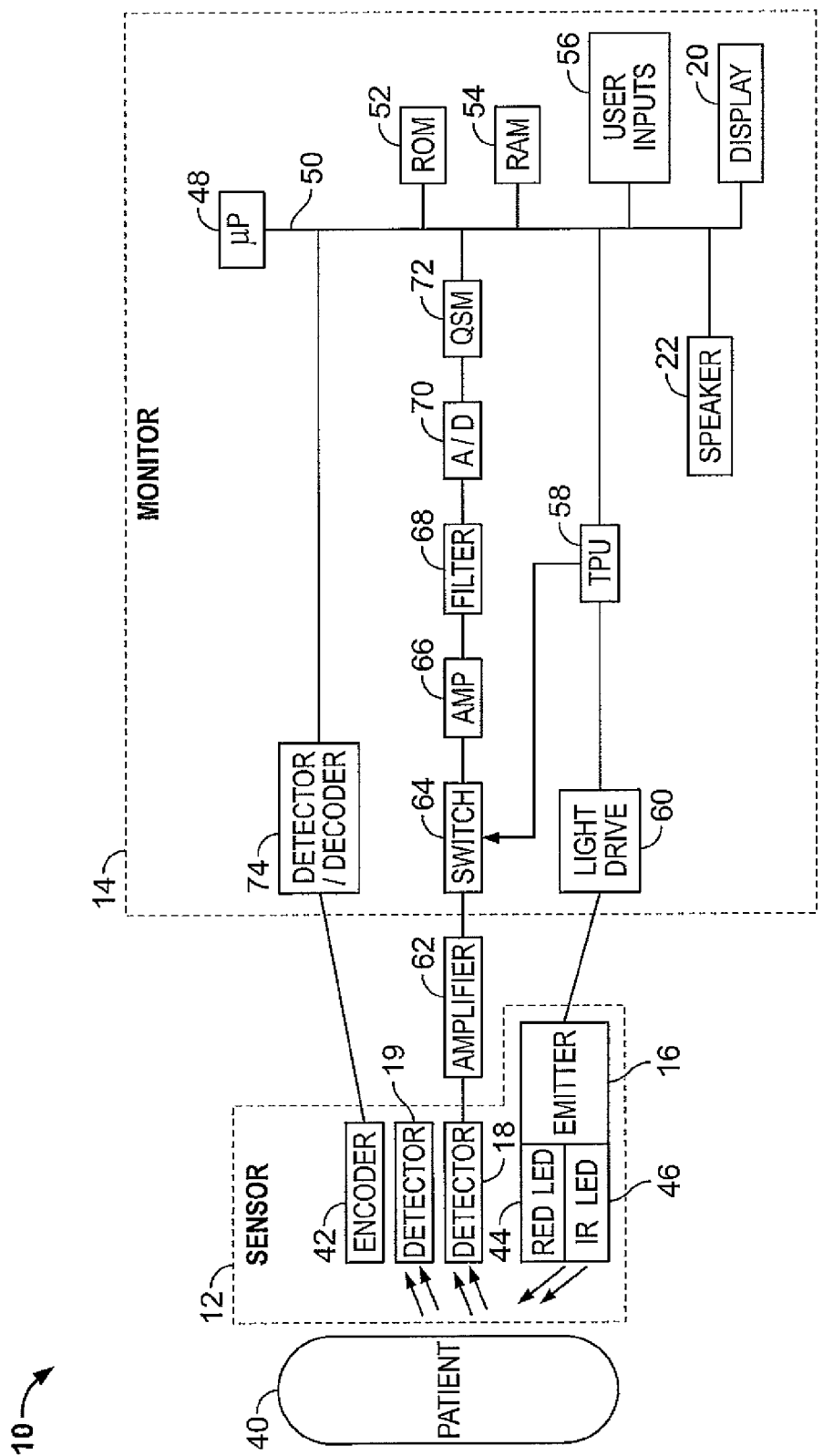
FIG. 2 is a block diagram of the illustrative oximetry system of FIG. 1 coupled to a patient in accordance with an embodiment.

FIG. 2 is a block diagram of an oximetry system, such as oximetry system 10 of FIG. 1, which may be coupled to a patient 40 in accordance with an embodiment. Certain illustrative components of sensor 12 and monitor 14 are illustrated in FIG. 2. Sensor 12 may include emitters 16, detectors 18 and 19, and encoder 42. In the embodiment shown, emitters 16 may be configured to emit at least two wavelengths of light (e.g., RED and IR) into a patient's tissue 40. Hence, emitters 16 may include a RED light emitting light source such as RED light emitting diode (LED) 44 and an IR light emitting light source such as IR LED 46 for emitting light into the patient's tissue 40 at the wavelengths used to calculate the patient's physiological parameters. In one embodiment, the RED wavelength may be between about 600 nm and about 700 nm, and the IR wavelength may be between about 700 nm and about 1000 nm. In embodiments where a sensor array is used in place of single sensor, each sensor may be configured to emit a single wavelength. For example, a first sensor emits only a RED light while a second only emits an IR light. Detectors 18 and 19 may be chosen to be specifically sensitive to the chosen targeted energy spectrum of the emitters 16.

In an embodiment, detectors 18 and 19 may be configured to detect the intensity of light at the RED and IR wavelengths. Alternatively, each sensor in the array may be configured to detect an intensity of a single wavelength. In operation, light may enter detectors 18 and 19 after passing through the patient's tissue 40. Detectors 18 and 19 may convert the intensity of the received light into an electrical signal. The light intensity is directly related to the absorbance and/or reflectance of light in the tissue 40. That is, when more light at a certain wavelength is absorbed or reflected, less light of that wavelength is received from the tissue by the detectors 18 and 19. After converting the received light to an electrical signal, detectors 18 and 19 may send the signal to monitor 14, where physiological parameters may be calculated based on the absorption of the RED and IR wavelengths in the patient's tissue 40.

In an embodiment, encoder 42 may contain information about sensor 12, such as what type of sensor it is (e.g., whether the sensor is intended for placement on a forehead or digit) and the wavelengths of light emitted by emitters 16. This information may be used by monitor 14 to select appropriate algorithms, lookup tables and/or calibration coefficients stored in monitor 14 for calculating the patient's physiological parameters.

Encoder 42 may contain information specific to patient 40, such as, for example, the patient's age, weight, and diagnosis. This information may allow monitor 14 to determine, for example, patient-specific threshold ranges in which the patient's physiological parameter measurements should fall and to enable or disable additional physiological parameter algorithms. Encoder 42 may, for instance, be a coded resistor which stores values corresponding to the type of sensor 12 or the type of each sensor in the sensor array, the wavelengths of light emitted by emitters 16 on each sensor of the sensor array, and/or the patient's characteristics. In another embodiment, encoder 42 may include a memory on which one or more of the following information may be stored for communication to monitor 14: the type of the sensor 12; the wavelengths of light emitted by emitters 16; the particular wavelength each sensor in the sensor array is monitoring; a signal threshold for each sensor in the sensor array; any other suitable information; or any combination thereof.

In an embodiment, signals from detectors 18 and 19 and encoder 42 may be transmitted to monitor 14. In the embodiment shown, monitor 14 may include a general-purpose microprocessor 48 connected to an internal bus 50. Microprocessor 48 may be adapted to execute software, which may include an operating system and one or more applications, as part of performing the functions described herein. Also connected to bus 50 may be a read-only memory (ROM) 52, a random access memory (RAM) 54, user inputs 56, display 20, and speaker 22.

RAM 54 and ROM 52 are illustrated by way of example, and not limitation. Any suitable computer-readable media may be used in the system for data storage. Computer-readable media are capable of storing information that can be interpreted by microprocessor 48. This information may be data or may take the form of computer-executable instructions, such as software applications, that cause the microprocessor to perform certain functions and/or computer-implemented methods. Depending on the embodiment, such computer-readable media may include computer storage media and communication media. Computer storage media may include volatile and non-volatile, removable and non-removable media implemented in any method or technology for storage of information such as computer-readable instructions, data structures, program modules or other data. Computer storage media may include, but is not limited to, RAM, ROM, EPROM, EEPROM, flash memory or other solid state memory technology, CD-ROM, DVD, or other optical storage, magnetic cassettes, magnetic tape, magnetic disk storage or other magnetic storage devices, or any other medium which can be used to store the desired information and which can be accessed by components of the system.

In the embodiment shown, a time processing unit (TPU) 58 may provide timing control signals to a light drive circuitry 60, which may control when emitters 16 are illuminated and multiplexed timing for the RED LED 44 and the IR LED 46. TPU 58 may also control the gating-in of signals from detectors 18 and 19 through an amplifier 62 and a switching circuit 64. These signals are sampled at the proper time, depending upon which light source is illuminated. The received signals from detectors 18 and 19 may be passed through an amplifier 66, a low pass filter 68, and an analog-to-digital converter 70. The digital data may then be stored in a queued serial module (QSM) 72 (or buffer) for later downloading to RAM 54 as QSM 72 fills up. In one embodiment, there may be multiple separate parallel paths having amplifier 66, filter 68, and A/D converter 70 for multiple light wavelengths or spectra received and for multiple detectors.

In an embodiment, microprocessor 48 may determine the patient's physiological parameters, such as SpO$_2$, regional oximetry, and pulse rate, using various algorithms and/or look-up tables based on the value of the received signals and/or data corresponding to the light received by detectors 18 and 19. Signals corresponding to information about patient 40, and particularly about the intensity of light emanating from a patient's tissue over time, may be transmitted from encoder 42 to a decoder 74. These signals may include, for example, encoded information relating to patient characteristics. Decoder 74 may translate these signals to enable the microprocessor to determine the thresholds based on algorithms or look-up tables stored in ROM 52. User inputs 56 may be used to enter information about the patient, such as age, weight, height, diagnosis, medications, treatments, and so forth. In an embodiment, display 20 may exhibit a list of values which may generally apply to the patient, such as, for example, age ranges or medication families, which the user may select using user inputs 56.

The optical signal through the tissue can be degraded by noise, among other sources. One source of noise is ambient light that reaches the light detector. Another source of noise is electromagnetic coupling from other electronic instruments. Movement of the patient also introduces noise and affects the signal. For example, the contact between the detector and the skin, or the emitter and the skin, can be temporarily disrupted when movement causes either to move away from the skin. In addition, because blood is a fluid, it responds differently than the surrounding tissue to inertial effects, thus resulting in momentary changes in volume at the point to which the oximeter probe is attached.

Noise (e.g., from patient movement) can degrade a pulse oximetry signal relied upon by a physician, without the physician's awareness. This is especially true if the monitoring of the patient is remote, the motion is too small to be observed, or the doctor is watching the instrument or other parts of the patient, and not the sensor site. Processing oximetry (i.e., PPG) signals may involve operations that reduce the amount of noise present in the signals or otherwise identify noise components in order to prevent them from affecting measurements of physiological parameters derived from the PPG signals.

It will be understood that the present disclosure is applicable to any suitable signals and that PPG signals are used merely for illustrative purposes. Those skilled in the art will recognize that the present disclosure has wide applicability to other signals including, but not limited to other biosignals (e.g., electrocardiogram, electroencephalogram, electrogastrogram, electromyogram, heart rate signals, pathological sounds, ultrasound, or any other suitable biosignal), dynamic signals, non-destructive testing signals, condition monitoring signals, fluid signals, geophysical signals, astronomical signals, electrical signals, financial signals including financial indices, sound and speech signals, chemical signals, meteorological signals including climate signals, and/or any other suitable signal, and/or any combination thereof.

In one embodiment, a PPG signal may be transformed using a continuous wavelet transform. Information derived from the transform of the PPG signal (i.e., in wavelet space) may be used to provide measurements of one or more physiological parameters.

The continuous wavelet transform of a signal x(t) in accordance with the present disclosure may be defined as $$T(a, b) = \frac{1}{\sqrt{a}} \int_{-\infty}^{+\infty} x(t)\psi^*\left(\frac{t-b}{a}\right) dt \quad (9)$$

where $\psi^*(t)$ is the complex conjugate of the wavelet function $\psi(t)$, a is the dilation parameter of the wavelet and b is the location parameter of the wavelet. The transform given by equation (9) may be used to construct a representation of a signal on a transform surface. The transform may be regarded as a time-scale representation. Wavelets are composed of a range of frequencies, one of which may be denoted as the characteristic frequency of the wavelet, where the characteristic frequency associated with the wavelet is inversely proportional to the scale a. One example of a characteristic frequency is the dominant frequency. Each scale of a particular wavelet may have a different characteristic frequency. The underlying mathematical detail required for the implementation within a time-scale can be found, for example, in Paul S. Addison, The Illustrated Wavelet Transform Handbook (Taylor & Francis Group 2002), which is hereby incorporated by reference herein in its entirety.

The continuous wavelet transform decomposes a signal using wavelets, which are generally highly localized in time. The continuous wavelet transform may provide a higher resolution relative to discrete transforms, thus providing the ability to garner more information from signals than typical frequency transforms such as Fourier transforms (or any other spectral techniques) or discrete wavelet transforms. Continuous wavelet transforms allow for the use of a range of wavelets with scales spanning the scales of interest of a signal such that small scale signal components correlate well with the smaller scale wavelets and thus manifest at high energies at smaller scales in the transform. Likewise, large scale signal components correlate well with the larger scale wavelets and thus manifest at high energies at larger scales in the transform. Thus, components at different scales may be separated and extracted in the wavelet transform domain. Moreover, the use of a continuous range of wavelets in scale and time position allows for a higher resolution transform than is possible relative to discrete techniques.

In addition, transforms and operations that convert a signal or any other type of data into a spectral (i.e., frequency) domain necessarily create a series of frequency transform values in a two-dimensional coordinate system where the two dimensions may be frequency and, for example, amplitude. For example, any type of Fourier transform would generate such a two-dimensional spectrum. In contrast, wavelet transforms, such as continuous wavelet transforms, are required to be defined in a three-dimensional coordinate system and generate a surface with dimensions of time, scale and, for example, amplitude. Hence, operations performed in a spectral domain cannot be performed in the wavelet domain; instead the wavelet surface must be transformed into a spectrum (i.e., by performing an inverse wavelet transform to convert the wavelet surface into the time domain and then performing a spectral transform from the time domain). Conversely, operations performed in the wavelet domain cannot be performed in the spectral domain; instead a spectrum must first be transformed into a wavelet surface (i.e., by performing an inverse spectral transform to convert the spectral domain into the time domain and then performing a wavelet transform from the time domain). Nor does a cross-section of the three-dimensional wavelet surface along, for example, a particular point in time equate to a frequency spectrum upon which spectral-based techniques may be used. At least because wavelet space includes a time dimension, spectral techniques and wavelet techniques are not interchangeable. It will be understood that converting a system that relies on spectral domain processing to one that relies on wavelet space processing would require significant and fundamental modifications to the system in order to accommodate the wavelet space processing (e.g., to derive a representative energy value for a signal or part of a signal requires integrating twice, across time and scale, in the wavelet domain while, conversely, one integration across frequency is required to derive a representative energy value from a spectral domain). As a further example, to reconstruct a temporal signal requires integrating twice, across time and scale, in the wavelet domain while, conversely, one integration across frequency is required to derive a temporal signal from a spectral domain. It is well known in the art that, in addition to or as an alternative to amplitude, parameters such as energy density, modulus, phase, among others may all be generated using such transforms and that these parameters have distinctly different contexts and meanings when defined in a two-dimensional frequency coordinate system rather than a three-dimensional wavelet coordinate system. For example, the phase of a Fourier system is calculated with respect to a single origin for all frequencies while the phase for a wavelet system is unfolded into two dimensions with respect to a wavelet's location (often in time) and scale.

The energy density function of the wavelet transform, the scalogram, is defined as $$S(a,b) = |T(a,b)|^2 \quad (10)$$

where '||' is the modulus operator. The scalogram may be resealed for useful purposes. One common resealing is defined as $$S_R(a, b) = \frac{|T(a, b)|^2}{a} \quad (11)$$

and is useful for defining ridges in wavelet space when, for example, the Morlet wavelet is used. Ridges are defined as the locus of points of local maxima in the plane. Any reasonable definition of a ridge may be employed in the method. Also included as a definition of a ridge herein are paths displaced from the locus of the local maxima. A ridge associated with only the locus of points of local maxima in the plane are labeled a "maxima ridge".

For implementations requiring fast numerical computation, the wavelet transform may be expressed as an approximation using Fourier transforms. Pursuant to the convolution theorem, because the wavelet transform is the cross-correlation of the signal with the wavelet function, the wavelet transform may be approximated in terms of an inverse FFT of the product of the Fourier transform of the signal and the Fourier transform of the wavelet for each required a scale and then multiplying the result by $\sqrt{a}$.

In the discussion of the technology which follows herein, the "scalogram" may be taken to include all suitable forms of resealing including, but not limited to, the original unsealed wavelet representation, linear resealing, any power of the modulus of the wavelet transform, or any other suitable resealing. In addition, for purposes of clarity and conciseness, the term "scalogram" shall be taken to mean the wavelet transform, T(a,b) itself, or any part thereof. For example, the real part of the wavelet transform, the imaginary part of the wavelet transform, the phase of the wavelet transform, any other suitable part of the wavelet transform, or any combination thereof is intended to be conveyed by the term "scalogram".

A scale, which may be interpreted as a representative temporal period, may be converted to a characteristic frequency of the wavelet function. The characteristic frequency associated with a wavelet of arbitrary a scale is given by $$f = \frac{f_c}{a} \quad (12)$$

where $f_c$, the characteristic frequency of the mother wavelet (i.e., at a=1), becomes a scaling constant and f is the representative or characteristic frequency for the wavelet at arbitrary scale a.

Any suitable wavelet function may be used in connection with the present disclosure. One of the most commonly used complex wavelets, the Morlet wavelet, is defined as:

$$\psi(t) = \pi^{-1/4}(e^{j2\pi f_0 t} - e^{-(2\pi f_0)^2/2})e^{-t^2/2} \quad (13)$$

where $f_0$ is the central frequency of the mother wavelet. The second term in the parenthesis is known as the correction term, as it corrects for the non-zero mean of the complex sinusoid within the Gaussian window. In practice, it becomes negligible for values of $f_0 \gg 0$ and can be ignored, in which case, the Morlet wavelet can be written in a simpler form as $$\psi(t) = \frac{1}{\pi^{1/4}} e^{j2\pi f_0 t} e^{-t^2/2} \quad (14)$$

This wavelet is a complex wave within a scaled Gaussian envelope. While both definitions of the Morlet wavelet are included herein, the function of equation (14) is not strictly a wavelet as it has a non-zero mean (i.e., the zero frequency term of its corresponding energy spectrum is non-zero). However, it will be recognized by those skilled in the art that equation (14) may be used in practice with $f_0 \gg 0$ with minimal error and is included (as well as other similar near wavelet functions) in the definition of a wavelet herein. A more detailed overview of the underlying wavelet theory, including the definition of a wavelet function, can be found in the general literature. Wavelet decomposition of PPG signals may be used to provide clinically useful information within a medical device. For example, wavelet decomposition of PPG signals may be used to calculate oxygen saturation values.

Figure 3:
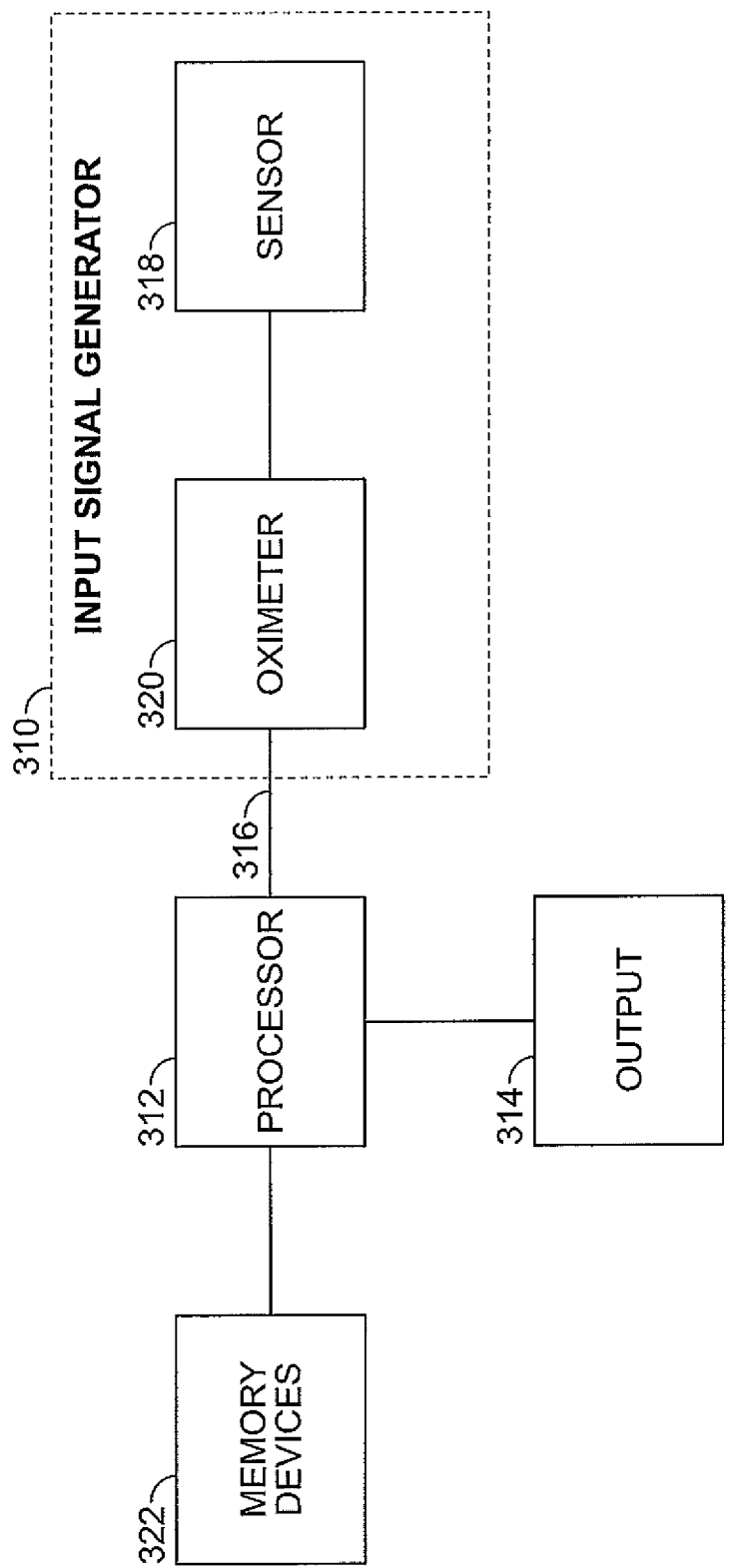
FIG. 3 is a block diagram of an illustrative oximeter system in accordance with an embodiment.

FIG. 3 is an illustrative oximeter system in accordance with an embodiment. In this embodiment, input signal generator 310 generates an input signal 316. As illustrated, input signal generator 310 may include oximeter 320 coupled to sensor 318 (e.g., sensor 401 in FIG. 4), which may provide as input signal 316, a PPG signal. It will be understood that input signal generator 310 may include any suitable signal source, signal generating data, signal generating equipment, or any combination thereof to produce signal 316. Signal 316 may be any suitable signal or signals, such as, for example, biosignals (e.g., electrocardiogram, electroencephalogram, electrogastrogram, electromyogram, heart rate signals, pathological sounds, ultrasound, or any other suitable biosignal), dynamic signals, non-destructive testing signals, condition monitoring signals, fluid signals, geophysical signals, astronomical signals, electrical signals, financial signals including financial indices, sound and speech signals, chemical signals, meteorological signals including climate signals, and/or any other suitable signal, and/or any combination thereof.

In this embodiment, signal 316 may be coupled to processor 312. Processor 312 may be any suitable software, firmware, and/or hardware, and/or combinations thereof for processing signal 316. For example, processor 312 may include one or more hardware processors (e.g., integrated circuits), one or more software modules, computer-readable media such as memory, firmware, or any combination thereof. Processor 312 may, for example, be a computer or may be one or more chips (i.e., integrated circuits). Processor 312 may perform the calculations associated with determining $SpO_2$ and regional blood oxygen saturation. Processor 312 may perform any suitable signal processing (including pre-processing) of signal 316 to filter signal 316, such as any suitable band-pass filtering, adaptive filtering, closed-loop filtering, and/or any other suitable filtering, and/or any combination thereof.

Processor 312 may be coupled to one or more memory devices 322 or incorporate one or more memory devices such as any suitable volatile memory device (e.g., RAM, registers, etc.), non-volatile memory device (e.g., ROM, EPROM, magnetic storage device, optical storage device, flash memory, etc.), or both. The memory may be used by processor 312 to, for example, store data corresponding to the processed input signal 316, such as data representing a scalogram generated using a continuous wavelet transform. In one embodiment, data representing the scalogram may be stored in RAM or memory internal to processor 312 as any suitable three-dimensional data structure such as a three-dimensional array that represents the scalogram as energy levels in a time-scale plane. Any other suitable data structure may be used to store data representing a scalogram.

Processor 312 may be coupled to output 314. Output 314 may be any suitable output device such as, for example, one or more medical devices (e.g., a medical monitor that displays various physiological parameters, a medical alarm, or any other suitable medical device that either displays physiological parameters or uses the output of processor 312 as an input), one or more display devices (e.g., monitor, PDA, mobile phone, any other suitable display device, or any combination thereof), one or more audio devices, one or more memory devices (e.g., hard disk drive, flash memory, RAM, optical disk, any other suitable memory device, or any combination thereof), one or more printing devices, any other suitable output device, or any combination thereof.

It will be understood that the oximeter system of FIG. 3 may be incorporated into system 10 (FIGS. 1 and 2) in which, for example, input signal generator 310 may be implemented as parts of sensor 12 and monitor 14 and processor 312 may be implemented as part of monitor 14.

Figure 4:
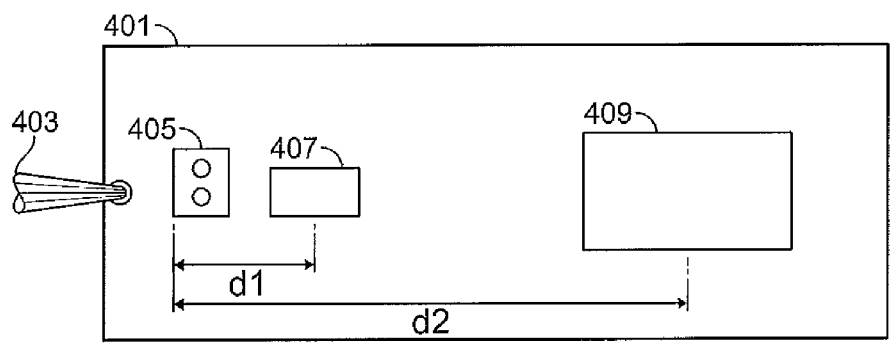
FIG. 4 is a bottom view of a sensor, showing features of a side that makes contact with a patient in accordance with an embodiment.

FIG. 4 is a bottom view of sensor 401, showing features of a side that makes contact with a patient in accordance with an embodiment. Sensor 401 may include light detectors 407 and 409 and light emitters 405. Emitters 405 may include two or more light emitters. In an embodiment, emitters 405 may be configured to emit at least two wavelengths of light (e.g., RED and IR) into a patient's tissue. Hence, emitters 405 may include a RED light emitting light source such as a RED light emitting diode (LED) and an IR light emitting light source such as an IR LED for emitting light into the patient's tissue at the wavelengths used to calculate the patient's physiological parameters. Further, emitters may include one or more optical fibers for directing light into the patient's tissue at the appropriate wavelengths. In an embodiment, the RED wavelength may be between about 600 nm and about 700 nm, and the IR wavelength may be between about 700 nm and about 1000 nm. In an embodiment, emitters 405 may be configured to emit a wideband light signal.

Detector 407 may be located at a distance d1 from emitters 405 and detector 409 may be located at a distance d2 from emitters 405, where distance d1 may be less than distance d2. For example, in an embodiment d1 may be 1 centimeter and d2 may be 4 centimeters. In an embodiment, emitters 405 may be placed in close proximity to detector 407, but may be much further from detector 409. In another embodiment, detector 407 and detector 409 may be placed in close proximity to each other. Detector 407 may be smaller in size than light detector 409 in order to equalize the differences in light intensity received/detected due to the distance of the detector from emitters 405. The size of a detector may be a function of a distance of the detector from an emitter. The size and/or the distance of a detector from an emitter may be a function of a desired mean path length of light traversing through human tissue. Although the use of two detectors and two emitters are depicted, any suitable number of detectors or emitters may be used. For example, four detectors may be used, each positioned at a different distance d from emitters 405. Sensor 401 may be configured to use a particular subset of the multiple detectors depending on the nature of the patient to which sensor 401 is connected. As another example, a single detector positioned at one distance d from emitters 405 may be used. In an embodiment, emitters 405 and detectors 407 and 409 may be arranged so that light from emitters 405 penetrates the tissue of a patient, in the region where sensor 401 is applied, and is reflected by the tissue into detectors 407 and 409.

Sensor 401 may be communicatively coupled to a monitor via a cable 403. However, in other embodiments, a wireless transmission device (not shown) or the like may be used instead of or in addition to cable 403. Cable 403 may provide an electrical path, a fiber optics path, or any other suitable wired communications path or combinations of such paths.

It will be understood that sensor 401 may be incorporated into system 10 (FIGS. 1 and 2) and/or the oximeter system of FIG. 3 in which, for example, detectors 407 and 409 and light emitters 405 may be implemented as parts of input signal generator 310, and/or parts of sensor 12, and cable 403 may be implemented as a part of cable 24.

Figure 5:
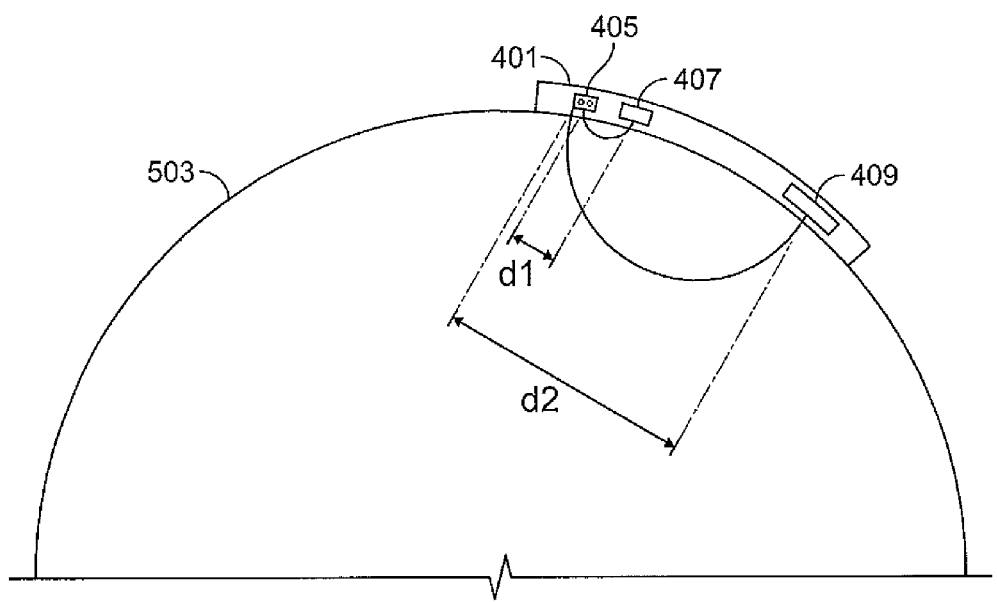
FIG. 5 depicts a view of a human cranium showing an application of the sensor of FIG. 4 on the forehead of a patient in accordance with an embodiment.

FIG. 5 depicts a view of a human cranium showing an application of sensor 401 on forehead 503 of a patient. As described above, sensor 401 may include light detectors 407 and 409 and light emitters 405. Detector 407, positioned a distance d1 from emitters 405, may receive light from these emitters. Detector 409, positioned a distance d2 from emitters 405, may also receive light from the emitters. Distance d1 may be substantially smaller than distance d2. A path length of light may be the distance that light travels through a material, such as, for example, human tissue located on the cranium of a patient. Due to distance d1 being smaller than distance d2, the mean path length of the received light from detector 407 may be shorter than the mean path length of received light from detector 409. Due to a shorter mean path length of the received light, detector 407 may receive light from emitters 405 after the light has passed through a few amount or layers of tissue in a region of a patient (e.g., the patient's forehead including the outer skin, the tissue covering the skull, and the skull). Due to a longer mean path length of the received light, detector 409 may receive light from emitters 405 after the light has passed through a substantially larger amount of tissue (e.g. including brain tissue) including the few layers of tissue through which the light received by detector 407 passed.

In an embodiment, the information (i.e., light intensity) received by detector 407 and the information received by detector 409 may be used to calculate a regional blood oxygen saturation and the information received by only one of detectors 407 and 409 may be used to calculate a pulse (e.g., arterial) blood oxygen saturation. In an embodiment, the information received by detector 407 and the information received by detector 409 may be used to calculate both a regional blood oxygen saturation and a pulse blood oxygen saturation. In some embodiments only one of a regional blood oxygen saturation and a pulse blood oxygen saturation may be calculated using the information received by detector 407 and/or the information received by detector 409. In some embodiments, others numbers of emitters and detectors may be used to calculate a regional blood oxygen saturation and/or a pulse blood oxygen saturation.

Figure 6A:
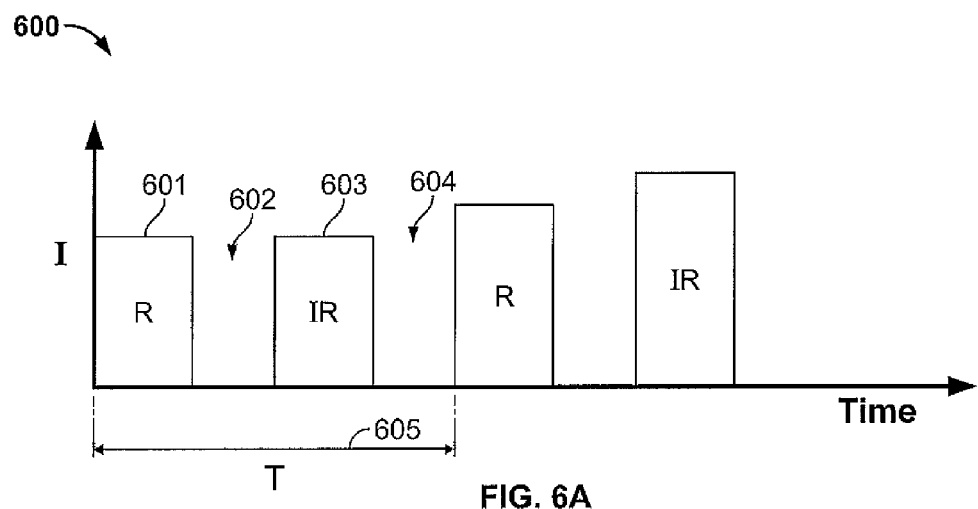
FIGS. 6(a) and 6(b) show illustrative timing diagrams of the intensity of RED and IR light emitted by a RED light and an IR light emitter, respectively, versus time in accordance with some embodiments.

FIG. 6(a) shows illustrative timing diagram 600 of the intensity (I) of RED and IR light emitted by a RED light and an IR light emitter, respectively, versus time in accordance with an embodiment. Timing diagram 600 includes a period 605 during which RED light impulse 601 and IR light impulse 603 are generated. Period 605 also includes intervals 602 and 604 when no light is generated by an emitter. The RED light impulse and the IR light impulse may be generated by, for example, emitters 405 of FIG. 4. As will be described below, the RED and IR light detected by the light detectors (e.g., detectors 407 and 409 of FIG. 4 or detectors 507 and 509 of FIG. 5) may be used to calculate a regional blood oxygen saturation and/or a pulse blood oxygen saturation. The time duration and intensity of RED light impulse 601, IR light impulse 603, and intervals 602 and 604 are merely illustrative and any suitable durations and intensities may be used. In an embodiment, the detected/received light associated with each of the impulses and intervals in period 605 may be used in the calculation of each of a regional blood oxygen saturation and a pulse blood oxygen saturation. In an embodiment the detected/received light associated with only a subset of the impulses and intervals in period 605 may be used in the calculation of each of a regional blood oxygen saturation and a pulse blood oxygen saturation. In some embodiments, the light received by light detectors associated with intervals 602 and 604 may assist in measuring ambient light-based noise. These measurements may assist in substantially improving the quality of the signal (e.g., RED and IR light signals) received/detected by a light detector and/or processed by the sensor, oximeter, or monitor circuitry. Period 605 may be changed to incorporate fewer or additional light impulses and/or intervals. This is discussed further with reference to FIG. 6(b), below.

Figure 6B:
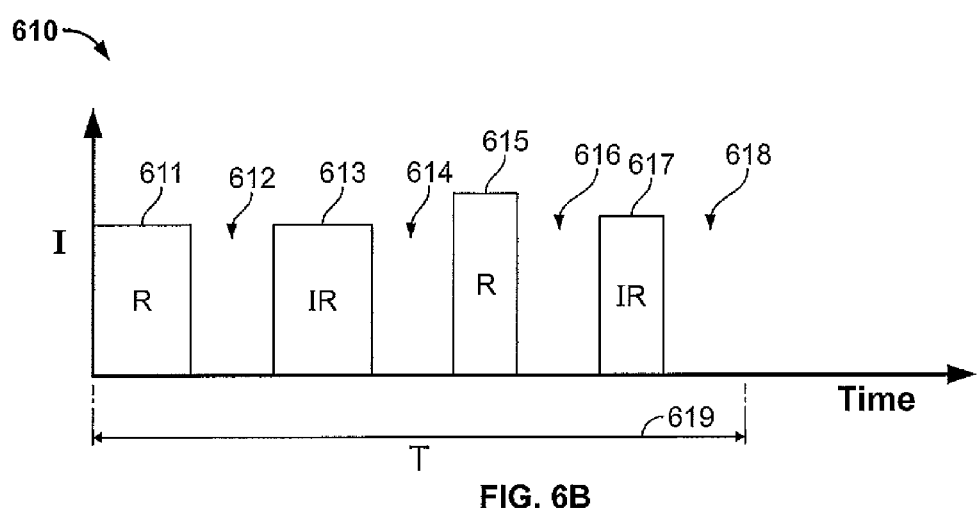

FIG. 6(b) shows illustrative timing diagram 610 of the intensity (I) of RED and IR light emitted by a RED light and an IR light emitter, respectively, versus time in accordance with an embodiment. Timing diagram 610 includes a period 619 during which RED light impulses 611 and 612 as well as IR light impulses 613 and 617 are each generated. Period 619 also includes intervals 612, 614, 616, and 618 when no light is generated by an emitter. The RED light impulse and the IR light impulse may be generated by, for example, emitters 405 of FIG. 4 or emitters 505 of FIG. 5. As will be described below, the RED or IR light detected by light detectors (e.g., detectors 407 and 409 of FIG. 4 or detectors 507 and 509 of FIG. 5) may be used to calculate a regional blood oxygen saturation and/or a pulse blood oxygen saturation. The time duration and intensity of RED light impulses 611 and 615, IR light impulses 613 and 617, and intervals 612, 614, 616, and 618, are merely illustrative and any suitable durations and intensities may be used. For example, the time duration of RED light impulse 615 may be different (e.g., shorter) than the time duration of RED light impulse 611 and the time duration of IR light impulse 617 may be different (e.g., shorter) than the time duration of IR light impulse 613. In addition, period 619 may be changed to incorporate fewer or additional light impulses and/or intervals. In an embodiment, the detected/received light associated with each of the impulses and intervals in period 619 may be used in the calculation of each of a regional blood oxygen saturation and a pulse blood oxygen saturation. In an embodiment the detected/received light associated with only a subset of the impulses and intervals in period 619 may be used in the calculation of each of a regional blood oxygen saturation and a pulse blood oxygen saturation. For example, the RED light impulse 611, IR light impulse 613, and intervals 612 and 614 may be used to calculate a regional blood oxygen saturation, while the RED light impulse 615, IR light impulse 617, and intervals 616 and 618 may be used to calculate a pulse blood oxygen saturation. In some embodiments, the light received by light detectors associated with intervals 612, 614, 616, and 618 may assist in measuring ambient light-based noise. These measurements may assist in improving the quality of the signal received/detected by a light detector and/or processed by sensor, oximeter, or monitor circuitry.

Figure 7:
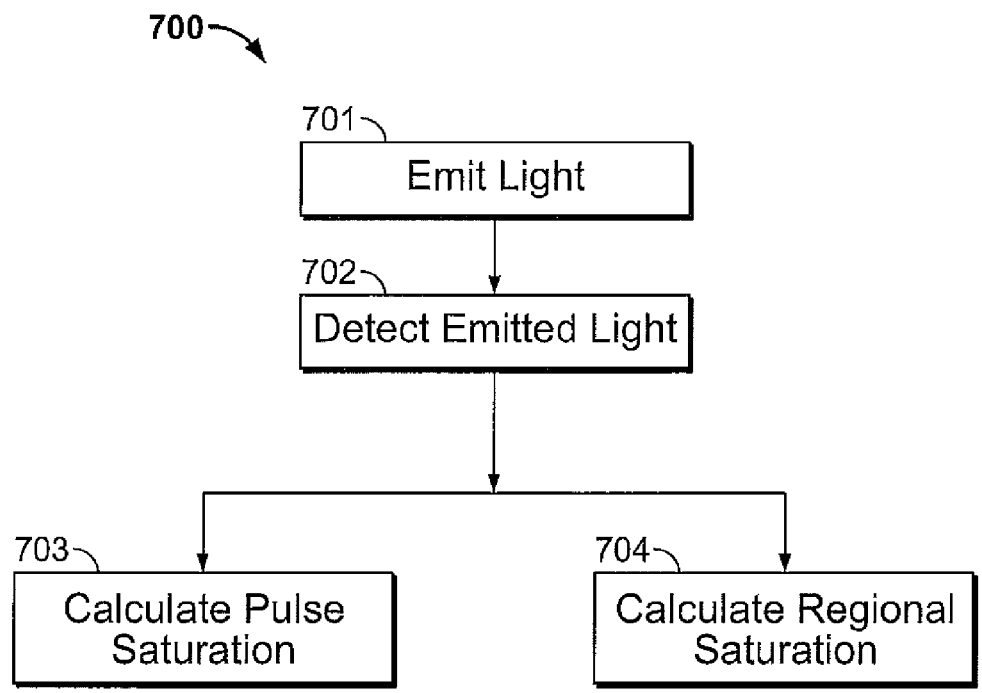
FIG. 7 is a flow chart of a process which includes illustrative steps involved in calculating oxygen saturation in accordance with an embodiment.

FIG. 7 is a flow chart of process 700 which includes illustrative steps involved in calculating oxygen saturation in accordance with some embodiments. The instructions to execute the steps of process 700 may be stored in, for example, memory devices such as RAM or ROM. Process 700 may be executed by, for example, processor 312 of FIG. 3. Process 700 includes steps 701, 702, 703, and 704.

At step 701, light may be emitted by light emitters (e.g., emitters 405 of FIG. 4 or emitters 505 of FIG. 5.) on a sensor (e.g., sensor 318 of FIG. 3, sensor 401 of FIG. 4, or sensor 501 of FIG. 5). The light may pass through a volume of tissue on a patient (e.g., a volume of a patient's cranium associated with a region close to the patient's forehead). In an embodiment, RED and IR light may be sequentially emitted. In an embodiment, a broadband light signal (e.g., a signal containing many wavelengths of the electromagnetic spectrum) may be emitted. Step 702 may then be executed or executed concurrently with step 701.

At step 702, light may be received/detected by light detectors (e.g., detectors 407 and/or 409 of FIG. 4 or detectors 507 and/or 509 of FIG. 5.) on a sensor (e.g., sensor 318 of FIG. 3, sensor 401 of FIG. 4, or sensor 501 of FIG. 5). The light may be received after it has passed through a volume of tissue on a patient (e.g., a volume of a patient's cranium associated with a region close to the patient's forehead). In an embodiment, RED and IR light may be detected. In an embodiment, the broadband light signal may be detected and filtered (e.g., using band-pass filtering techniques that make use of light filters associated with the light detectors) to acquire data pertaining to particular wavelengths of the electromagnetic spectrum. In an embodiment, the broadband light signal may be detected and later processed (e.g., using a monitor) to acquire particular wavelengths of data and/or types of information. In an embodiment, the detection of a light signal may be similar to the operation of a spectrometer. In an embodiment, the detector may include an optical fiber to direct the detected light to a distant point for analysis.

Steps 701 and 702 may be repeated, in any order, several times for different light signals. For example, the light may be emitted in accordance with timing diagram 600 of FIG. 6(a) or in accordance with timing diagram 610 of FIG. 6(b) or in any suitable timing of light impulses. Light may be detected after each emission of light by light emitters or during the absence of light emitted by light emitters.

Once light has been emitted, passed through human tissue, and received/detected, blood oxygen saturation may be calculated from the resulting PPG signals. Pulse blood oxygen saturation and regional blood oxygen may be calculated simultaneously at steps 703 and 704. Steps 703 and 704 may be executed individually, sequentially, or simultaneously.

At step 703, pulse (e.g., arterial) blood saturation may be calculated. At step 703, two PPG signals (e.g., RED and IR PPG signals) may be pre-processed and processed. The PPG signals may be generated from a detector that is in relatively "close" proximity to light emitters (i.e., light having a relatively short mean path length through human tissue, as discussed with relation to FIG. 5). For example, the light received/detected by "close" detector 407 of FIG. 4 or FIG. 5 may first undergo analog pre-processing and analog to digital conversion using an A/D converter, and may then be separately processed and/or filtered to optimally calculate pulse oximetry values. As another example, the light received/detected by "close" detector 407 of FIG. 4 or FIG. 5 may first undergo analog pre-processing and may then be separately processed (e.g., by separate analog to digital conversion for each of the regional oximetry and pulse oximetry using A/D converters) and/or filtered to optimally calculate pulse oximetry values. The PPG signals generated by detector 407 of FIG. 4 or FIG. 5 may be used to calculate pulse blood oxygen saturation. Alternatively, the PPG signals may be generated from a detector that is relatively far from the light emitters. The calculation of pulse oximetry values may use any suitable technique such as the techniques described above.

At step 704, regional blood oxygen saturation may be calculated. At step 704, PPG signals from the two detectors may be pre-processed and processed. For example, the light received/detected by "close" detector 407 and "far" detector 409 of FIG. 4 or FIG. 5 may first undergo analog pre-processing, analog to digital conversion using an A/D converter, and may then be separately processed and/or filtered to optimally calculate regional oximetry values. As another example, the light received/detected by "close" detector 407 and "far" detector 409 of FIG. 4 or FIG. 5 may first undergo analog pre-processing and may then be separately processed (e.g., by separate analog to digital conversion for each of the regional oximetry values and pulse oximetry values using A/D converters) and/or filtered to optimally calculate regional oximetry values. The light received/detected by "close" detector 407 and "far" detector 409 of FIG. 4 or FIG. 5 may be used in the calculation of regional oximetry values and/or regional blood oxygen saturation. The calculation of regional oximetry values may use any suitable technique such as the techniques described above. For example, the processing of the PPG signals may include subtracting the PPG signals from a "close" detector from the corresponding PPG signals from a "far" detector.

As discussed above, due to a shorter mean path length of the received light at the "close" detector, the light may only pass through a few layers of tissue in a region of a patient where the sensor is applied (e.g., outer skin of a forehead, the tissue covering the skull, and the skull). Due to a longer mean path length of the received light at the "far" detector, the light has passed through a substantially larger amount of tissue (e.g., including brain tissue) including the shallower layers of tissue through which the light received by the "close" detector passed. The received/detected light signals may be processed and these processed signals may be subtracted from each other in order to arrive at information about the additional tissue through which the light received at the "far" detector passed (e.g., only brain tissue) and with very little or no information about the tissue through which the light received at the "close" detector passed. The processed, subtracted signals may allow for the calculation of a regional blood saturation that pertains to the additional tissue through which the light received at the "far" detector passed. Using this procedure, at step 704, the oxygen saturation of a patient's blood within the venous, arterial and capillary systems of a region on a patient may be calculated.

After process 700 has been performed, the blood oxygen saturation of the venous systems or capillary systems underlying a patient's tissue may be determined from the resulting pulse blood oxygen saturation value and regional blood oxygen saturation value. For example, the pulse blood oxygen saturation value may be appropriately weighted and then subtracted from the regional blood saturation value after it has also been appropriately weighted. The weighting of each of the pulse and regional blood saturation values may be based on known ratios or may be empirically derived. As an example, if the $SpO_2$ measurement is 95 and the regional blood oxygen saturation is 65, and it is assumed that arterial blood is one-thirds of the blood in a region of interest (e.g., the forehead), then the venous and/or capillary blood saturation may be determined to be 50.

Figure 8:
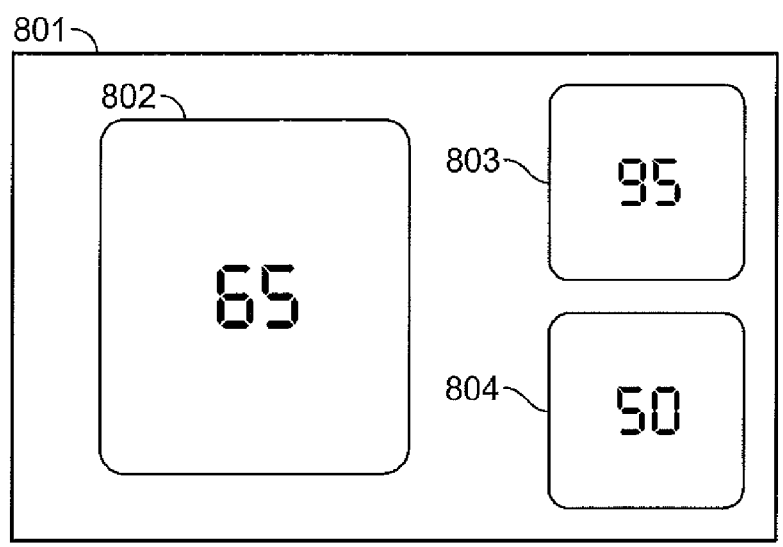
FIG. 8 is a front view of a display, showing the display of various calculated and/or derived blood oxygen saturation values.

FIG. 8 is a front view of display 801, showing various calculated and/or derived blood oxygen saturation values. Display 801 may be on the display 28 of FIG. 1 and/or on display 20 of FIG. 2. Values may be displayed on display 801 in display portions 802, 803, and/or 804. After process 700 of FIG. 7 has been performed, the resulting pulse blood oxygen saturation and regional blood oxygen saturation may be displayed simultaneously in a preconfigured portion of a display (e.g., display portions 802, 803, and/or 804). In addition the determined blood oxygen saturation of the venous systems or capillary systems may be displayed in a preconfigured portion of a display (e.g., in display portions 802, 803, and/or 804). Each of the displayed values for blood oxygen saturation may be in any size or color. For example, the regional blood oxygen saturation may be displayed in a relatively large size in a left portion of a display (e.g., display portion 802) while the pulse blood oxygen saturation and blood oxygen saturation of the venous systems and/or capillary systems may be displayed on the right side of the display (e.g., in display portions 803, and/or 804) in a relatively small size. The pulse blood oxygen saturation may be displayed on top (e.g., in display portion 803) of the venous and/or capillary blood oxygen saturation (e.g., in display portion 804). For example, the pulse blood oxygen saturation may be displayed in red and the venous and/or capillary blood oxygen saturation may be displayed in blue.

The display of blood oxygen saturation values in display 800 and the locations of display portions 802, 803, and 804 on display 801 are merely illustrative and any suitable sizes and locations may be used.

Accordingly, it will be understood that by using at least a single sensor, which has two or more emitters and one or more detectors, it is possible to calculate both a pulse and regional blood oxygen saturation simultaneously. It will also be understood that the above method may be implemented using any human-readable or machine-readable instructions on any suitable system or apparatus, such as those described herein.

The foregoing is merely illustrative of the principles of this disclosure and various modifications may be made by those skilled in the art without departing from the scope and spirit of the disclosure. The following claims may also describe various aspects of this disclosure.

What is claimed is:

1. A method for calculating blood oxygen saturations, the method comprising:
   emitting a plurality of light signals from light emitters;
   receiving a first light signal at a first light detector, wherein the received first light signal comprises a first set of impulses corresponding to a first wavelength of emitted light emitted from the light emitters and a second set of impulses corresponding to a second wavelength of light emitted from the light emitters;
   receiving a second light signal at a second light detector;
   calculating a pulse blood oxygen saturation based on a first subset of the first and second sets of impulses of the received first light signal, using a processor, wherein the calculation of pulse blood oxygen saturation is not based on a second subset of the first and second sets of impulses; and calculating a regional blood oxygen saturation based on the second subset of the first and second sets of impulses and the received second light signal, using a processor, wherein the calculating a pulse blood oxygen saturation and the calculating a regional blood oxygen saturation are done substantially simultaneously.

2. The method of claim 1, wherein the first light detector is positioned at a first distance from the light emitters and the second light detector is positioned at a second distance, greater than the first distance, from the light emitters.

3. The method of claim 1, wherein the first light detector is associated with a first mean path length and wherein the second light detector is associated with a second mean path length, greater than the first mean path length.

4. The method of claim 1, wherein the emitting comprises emitting a first wavelength of light from light emitters for a first duration and emitting a second wavelength of light from light emitters for a second duration.

5. The method of claim 4, wherein the first wavelength is smaller than the second wavelength and the first duration is greater than the second duration.

6. The method of claim 1, wherein the plurality of light signals comprises a RED light signal and an IR light signal.

7. The method of claim 1, wherein the plurality of light signals comprises broadband light signals.

8. The method of claim 1, wherein the calculating the pulse blood oxygen saturation comprises a ratio-of-ratios technique based on a light intensity and wherein the calculating the regional blood oxygen saturation involves a differencing technique based on the light intensity.

9. The method of claim 1, wherein the calculating the pulse blood oxygen saturation comprises pre-processing the received first light signal using a first technique and the calculating the regional blood oxygen saturation comprises pre-processing the received first light signal using a second technique.

10. The method of claim 1, wherein the calculated pulse blood oxygen saturation and the calculated regional blood oxygen saturation are used to calculate a venous/capillary blood oxygen saturation.

11. A system for calculating blood oxygen saturations, the system comprising:

light emitters capable of emitting a plurality of light signals;

a first light detector capable of receiving a first light signal, wherein the received first light signal comprises a first set of impulses corresponding to a first wavelength of emitted light emitted from the light emitters and a second set of impulses corresponding to a second wavelength of light emitted from the light emitters;

a second light detector capable of receiving a second light signal;

a processor capable of calculating a pulse blood oxygen saturation based on a first subset of the first and second sets of impulses of the received first light signal, wherein the calculation of pulse blood oxygen saturation is not based on a second subset of the first and second sets of impulses; and a processor capable of calculating a regional blood oxygen saturation based on the second subset of the first and second sets of impulses and the received second light signal, wherein the processor is capable of calculating the pulse blood oxygen saturation and calculating the regional blood oxygen saturation substantially simultaneously.

12. The system of claim 11, wherein the first light detector is positioned at a first distance from the light emitters and the second light detector is positioned at a second distance, greater than the first distance, from the light emitters.

13. The system of claim 11, wherein the first light detector is associated with a first mean path length and wherein the second light detector is associated with a second mean path length, greater than the first mean path length.

14. The system of claim 11, wherein the light emitters are capable of emitting a first wavelength of light for a first duration and emitting a second wavelength of light from light emitters for a second duration.

15. The system of claim 14, wherein the first wavelength is smaller than the second wavelength and the first duration is greater than the second duration.

16. The system of claim 11, wherein the plurality of light signals comprises a RED light signal and an IR light signal.

17. The system of claim 11, wherein the plurality of light signals comprises broadband light signals.

18. The system of claim 11, wherein the processor is capable of calculating the pulse blood oxygen saturation using a ratio-of-ratios technique based on a light intensity and wherein the processor is capable of calculating the regional blood oxygen saturation using a differencing technique based on the light intensity.

19. The system of claim 11, wherein the processor is capable of pre-processing the received first light signal using a first technique and pre-processing the received first light signal using a second technique.

20. The system of claim 11, wherein the processor is capable of calculating a venous/capillary blood oxygen saturation using the pulse blood oxygen saturation and the regional blood oxygen saturation.

* * * * *